United States Patent
Wei et al.

(10) Patent No.: US 7,297,966 B2
(45) Date of Patent: Nov. 20, 2007

(54) UTILIZING AN INTEGRATED PLASMON DETECTOR TO MEASURE A METAL DEPOSIT ROUGHNESS ON A SEMICONDUCTOR SURFACE

(75) Inventors: David T. Wei, Malibu, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 268 days.

(21) Appl. No.: 11/205,782

(22) Filed: Aug. 16, 2005

(65) Prior Publication Data

US 2006/0050280 A1   Mar. 9, 2006

Related U.S. Application Data

(60) Provisional application No. 60/602,117, filed on Aug. 17, 2004, provisional application No. 60/602,061, filed on Aug. 17, 2004.

(51) Int. Cl.
*G01J 3/45* (2006.01)
*G01N 13/00* (2006.01)

(52) U.S. Cl. .............. 250/492.2; 250/397; 250/399; 356/445; 356/451; 345/87; 345/77

(58) Field of Classification Search ................. None
See application file for complete search history.

(56) References Cited

U.S. PATENT DOCUMENTS

| 4,482,779 A | 11/1984 | Anderson .................. 136/255 |
| 5,451,980 A * | 9/1995 | Simon et al. .................. 345/88 |
| 2006/0170926 A1* | 8/2006 | Wei et al. .................. 356/445 |

OTHER PUBLICATIONS

Ditlbacher, H., et al., "Efficiency of local light-plasmon coupling", *Applied Physics letters, AIP, American Institute of Physics*, vol. 83, No. 18, p. 3665 lefthand column, paragraph 3, p. 3667. lefthand column, paragraph 1, figures 1,3.

Jasperson, S.N., et al., "Photon-surface-plasmon coupling in thick Ag foils", *Physical Review USA*, vol. 188, No. 2, pp. 759-770 (Dec. 1969).

* cited by examiner

*Primary Examiner*—Nikita Wells
(74) *Attorney, Agent, or Firm*—Ladas & Parry LLP

(57) ABSTRACT

A method for monitoring the surface roughness of a metal, comprises impinging a laser beam onto the surface of a metal layer to induce the formation of a plasmon therein, and monitoring a current of decay electrons emitted by the plasmon.

9 Claims, 3 Drawing Sheets

UTILIZING AN INTEGRATED PLASMON DETECTOR TO MEASURE A METAL DEPOSIT ROUGHNESS ON A SEMICONDUCTOR SURFACE

CROSS-REFERENCE TO RELATED APPLIATIONS

This application claims the benefit of U.S. provisional Patent Application Ser. No. 60/602,117, filed Aug. 17, 2004 for "Using a Polaron Interaction Zone as an Interface to Integrate a Surface Plasmon Layer and a Semiconductor Detector" and U.S. provisional Patent Application Ser. No. 60/602,061, filed Aug. 17, 2004 for "Utilizing an Integrated Plasmon Detector to Measure a Metal Deposit Roughness on a Semiconductor Surface," both by David T. Wei and Axel Scherer, the disclosures of which are incorporated in their entirety herein by reference thereto. This application is filed on the same day as U.S. patent application Ser. No. 11/205,781, for "Using a Polaron Interaction Zone as an Interface to Integrate a Plasmon Layer and a Semiconductor Detector", also incorporated herein by reference in its entirety.

STATEMENT REGARDING FEDERALLY SPONSORED RESEARCH OR DEVELOPMENT

The present invention was supported in part by grant no. F49620-03-1-0418 from the United States Air Force Office of Scientific Research. The U.S. Government may have rights in any patent issuing on this application.

BACKGROUND

1. Field

The present disclosure relates to integrated plasmon detectors, and more particularly to employing such detectors to monitor the surface roughness of a metal deposit.

2. Related Art

Currently known and used methods of determining surface roughness revolve mainly around the use of microscopy, such as atomic force microscopy, scanning tunnel microscopy, and low energy scanning electron microscopy. Such techniques can achieve high resolution, but cannot be effectively used to monitor surface changes in real time. Such real time monitoring may be achieved through the use of piezoelectric crystals or optical reflection, but such techniques usually require comparatively large surface areas that are not practicable on a nano scale, and thus not adaptable to monitoring very fine surface roughness. The present disclosure addresses these needs and difficulties with a novel approach to surface roughness detection and monitoring.

SUMMARY

According to one embodiment described herein, a method for monitoring the surface roughness of a metal, comprises impinging a laser beam onto the surface of a metal layer to induce the formation of a plasmon therein, and monitoring a current of decay electrons emitted by the plasmon.

In further embodiments, the metal layer may be deposited on a buffer layer that may comprise a substantially non-conductive Π region, and the buffer layer may comprise any one or more of the group comprised of ZnSe, CdS, GaN, GaP, GaAs, and Si. In yet further embodiments, the decay electrons may be captured at a collector junction or semiconductor layer, and may also be passed through a layer of substantially non-light transmissive material prior to collection. The decay electrons may be slowed to thermal energy levels before capture. In a still further embodiment, an electric circuit may be connected between the semiconductor layer and the metal layer to conduct captured electrons to the top layer.

DESCRIPTION OF THE PREFERRED EMBODIMENTS

When a species of atoms (whether gas, liquid, or solid) is ionized into an equal number of free electrons and ionized atomic cores known as ions, the atoms are said to be in a plasma state. In an ideal undisturbed gaseous plasma, the density of free electrons is equal to that of the positively charged ions and the overall distribution of charge is equal, and thus neutral, throughout the plasma. When this distribution is disturbed, the electrons seek to restore their neutral positions through the combined effect of repulsion from other electrons and attraction from the uniform positive charge background of the ions. This will induce an oscillation in the electrons as they attempt to return to their neutral positions known as plasma oscillation. [The Feynman Lectures of Physics, R. P. Feynman et al., Addison Wesley, Reading, Mass. 1964, the entire contents of which are incorporated herein by reference.]

Figure 1A:
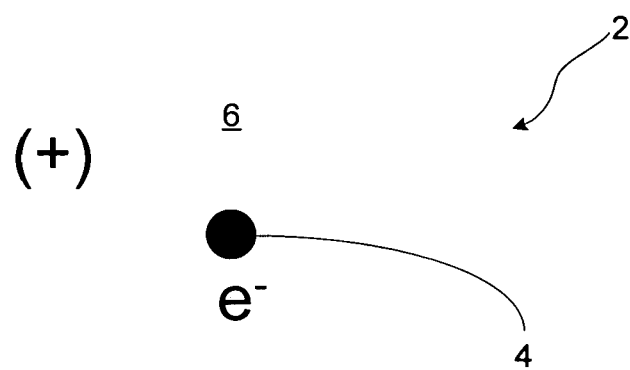
FIGS. 1(a)-1(c) are a diagram representation of a jellium particle, and the formation and destruction mechanisms for a jellium particle.

In a metal, the density of free electrons is much higher, and their temperature much lower, than in a gaseous plasma. These free electrons are thus a quantum gas and, when oscillating, form what is termed a plasmon. Free electrons oscillating at a common frequency are oscillating at plasmon frequencies that are generally very high, having a typical value on the order of $3 \times 10^{15}$ Hz (corresponding to a charge of about 12 eV). [Elementary Excitation in Solids, D. Pines, Benjamin, New York 1964; and Statistical Mechanics, R. P. Feynman, Addison Wesley, Reading, Mass. 1972; the entire contents of both of which are incorporated herein by reference.] For purposes of discussion and with reference to FIG. 1(a), whereas a plasmon is understood herein to refer to the state of quantum plasma in a solid, a jellium 2 is understood to mean a quasiparticle consisting of a negatively charged core 4 shielded by positive charges 6 gathered from the surrounding ions within a Fermi-Thomas radius $\lambda_{FT}$, which is comparable to the radius of a host atom in a metal lattice. The electron thus oscillates within this atom-sized sphere of positively-charge volume, evincing a high frequency and thus displacement that is small relative to the size of the sphere. When all such electrons oscillate in phase with one another, a standing plasmon wave arises (k=0), whereas a linear series of electrons having a definite phase relationship to one another correspond to a traveling plasmon wave having definite direction and mode numbers k (k≠0).

Figure 1B:
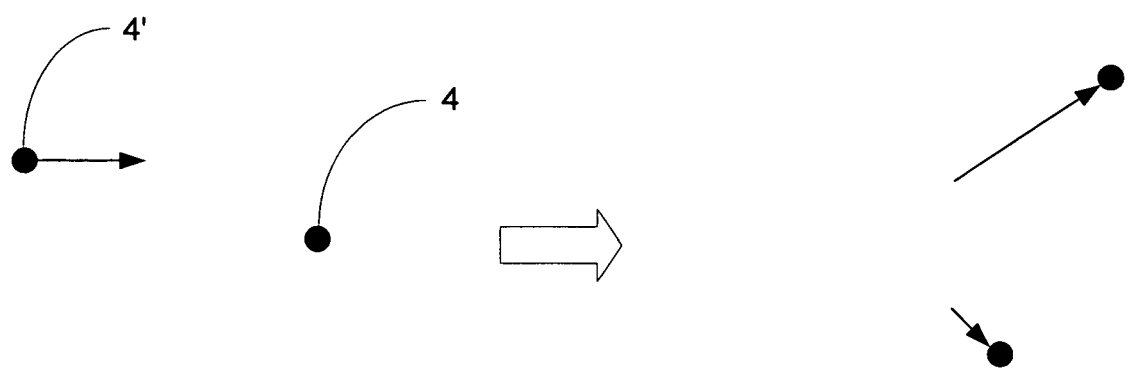
Figure 1C:
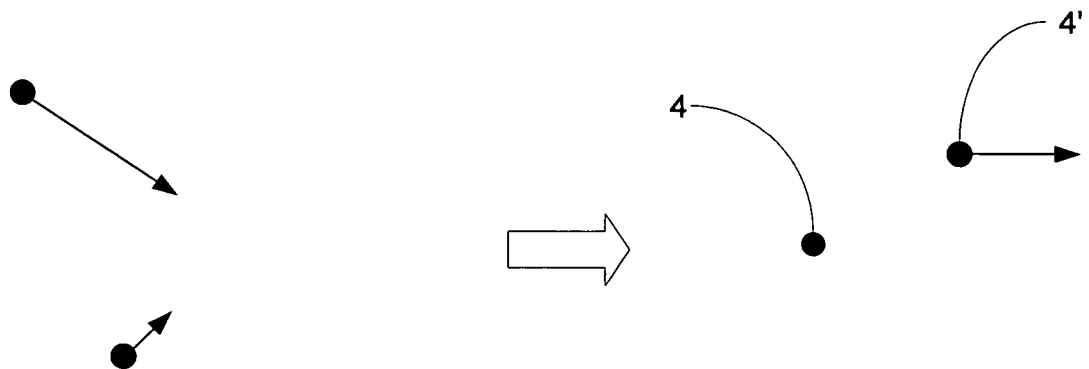

A quantum plasma in a solid also contains individual "hot" electrons that tend to interact (i.e. collide) with each other and with jelliums much more frequently that with the host ion lattice. When a hot electron 4' penetrates a jellium 2, as shown in FIG. 1(b), there are two negative electron charges 4, 4' inside a volume 6 of a unit of positive charge. This imbalance of charge leads the jellium to disintegrate by the expulsion of both electrons such that total momentum is conserved. Conversely, when two such hot electrons collide, as shown in FIG. 1(c), the result is a stationary jellium 2 at the point of impact and one free electron 4'. Molecular physics teaches us that the probabilities of these two opposite processes are equal.

When a metal is impinged upon by a laser pulse beam having a frequency below the plasmon frequency of the metal, electrons begin to be set in motion at randomly distributed frequencies lying between the laser beam and the plasmon frequencies (between $10^{15}$ and $3\times10^{15}$ Hz). Initially most of these electrons are free hot electrons, with few jelliums. These hot electrons tend to favor the creation of jelliums through their collisions, and thus the subgroup of collective electron plasmonic oscillations begins to build up in jelliums as energy is transferred from the laser beam to the plasmon system. Depending on the length of the laser pulse and the thickness of the metal, the plasmon oscillations may reach a peak maximum range, with free electron density as high as $10^{23}/cm^3$. These collective oscillations have a natural frequency or plasma frequency determined by the density of electrons in the neutral distribution $n_0$, and can be expressed as $$f = \left(\frac{1}{2\pi}\right)\sqrt{\frac{e^2 n_0}{\varepsilon_0 m_e}} \quad (1)$$

where e is the unit electron charge, $n_0$ is the neutral density of electrons in a plasma, $\varepsilon_0$ is the permittivity of vacuum, and $m_e$ is the unit electron mass.

When the laser beam ceases to impinge onto the metal, most jelliums continue to oscillate at their respective plasmon frequency characteristic of concentration and movement (mood number). When a jellium falls out of step with the whole class collective modes of existing plasmon oscillations, it drops out and an 'individual' hot electron (as opposite to a 'collective class' hot electron) results that eventually cools down to room temperature to become a thermal electron. However, if it does not pass through an adaptor layer to cool down quickly, the remaining heat will make detecting it functionally difficult.

Figure 2:
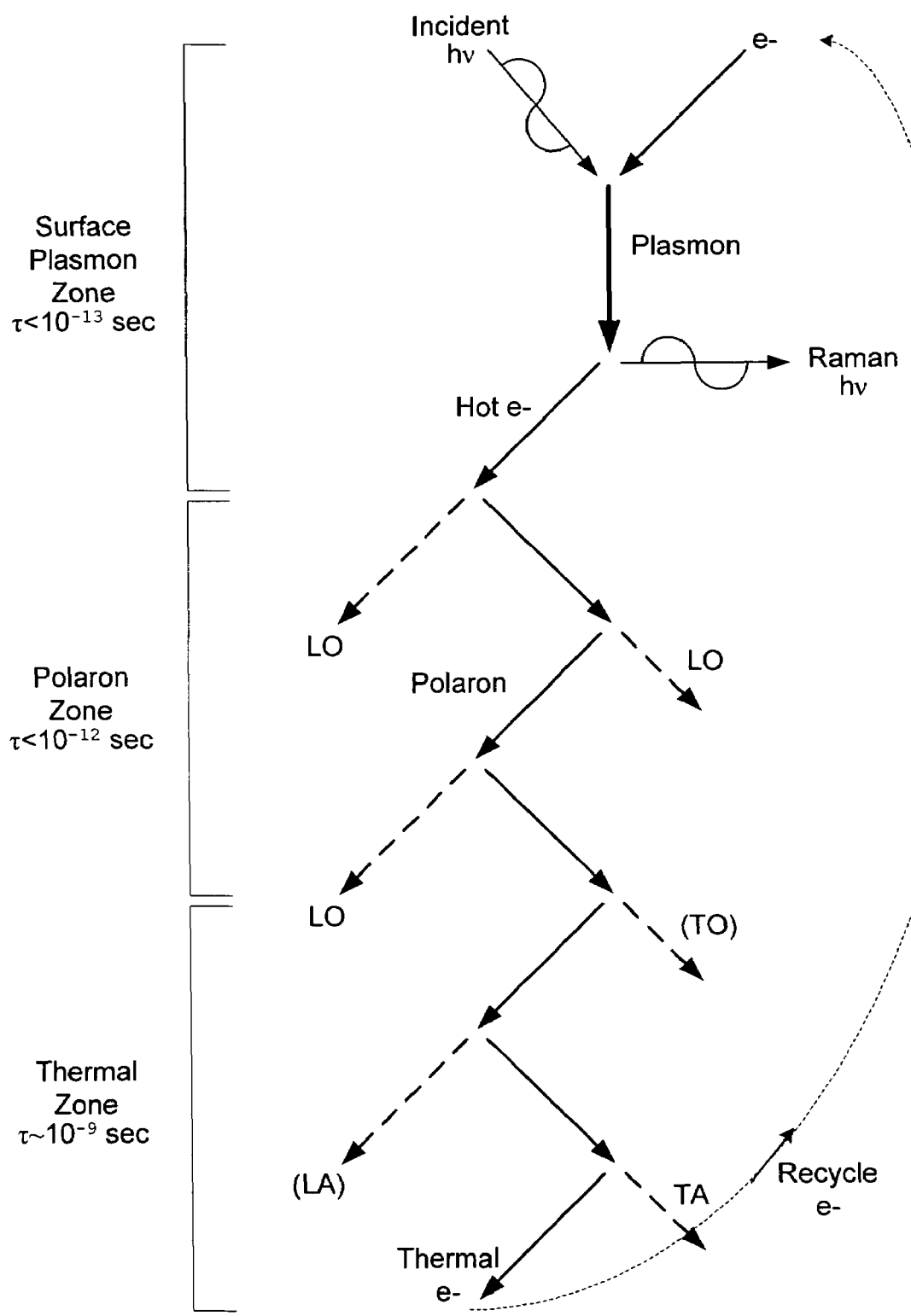
FIG. 2 is a Feynman diagram representation of a polaron decay scheme employed in embodiments described in the present disclosure.

Referring to FIG. 2, a Feynman diagram depicts the decays scheme of a jellium or plasmon particle. An incident photon laser pulse that strikes a conductive mass of material (such as silver, gold, or other metal) excites free electrons to set up a plasmon, which then decays by emitting a high-energy electron and a Raman scattering photon that is reflected back from the mass. Thus, conservation of momentum dictates that the matching high-energy electron travels in a generally opposite direction from that of the Raman photon, and away from the surface. As the plasmon decays after the pulse, and accumulation underneath the surface of such high-energy "hot" electrons of energy between 0.04 eV and 12 eV begins to collapse towards the interior of the conductive material and proceed to interact with the ionic lattice atoms of this material. If this material is polar (that is, strongly ionic in nature), these high-energy electrons are quickly quenched. This stream of high-energy electrons traveling at high velocity through such a polar lattice has a distortion affect upon the lattice that takes the form of a wave (similar, on a broad conceptual level, to a breeze flowing through a grass field). As each high-energy electron moves through the atomic lattice, it drags the lattice disturbance with it and interacts with the ionic charges in the lattice, thereby forming a new composite particle known as a polaron.

More specifically, polarons are formed by the charge coupling of a high-energy electron with the ionic charges from the solid atomic lattice, taking the form of a hot and heavy composite particle, or eigenstate, moving through the lattice. Through the charge coupling between the hot electron and the lattice ions, the electron sheds its kinetic energy to the ionic lattice one quantum per each interaction. Each such quantum of energy imparted to the lattice causes the lattice to vibrate in unison, thereby giving rise to a "wake" behind the high-energy electron. Each quantum of such lattice vibration is known as a phonon, and a high-energy electron dragging a wake of phonons behind it forms a polaron. As each phonon breaks away from the polaron, the polaron loses a quantum of energy and recoils at a random angle until it eventually loses all of its kinetic energy and becomes a "cold," or thermal, electron (having energies on the order of 0.04 eV, or room temperature). ["Oscillatory and Excitation Spectra of CdS and ZnSe," Proc. $3^{rd}$. Int. Conf. On Photoconductivity, D. T. Y. Wei et al., pp. 343-350, edited by E. M. Pell, Pergamon, N.Y., 1973, the entire contents of which are incorporated herein by reference.]

With continued reference to FIG. 2, there are four basic types of phonons, as defined in Table I below.

TABLE I

| Wave Polarization Direction/<br>Displacement of Ions in Unit Cell | Longitudinal | Transverse |
|---|---|---|
| Along each other (Acoustic) | LA | TA |
| Opposite (Optical) | LO | TO |

The relative electron coupling strength of each of the above four types of phonons depends on the band structure and how polar the host material is (increasing across the Group IV, III-V, and II-VI sequence of semiconductors). For most popular optical crystals, the shortest emission time is for LO phonons (about $10^{-13}$ sec) and the longest emission time is for TA phonons (>$10^{-9}$ sec). The emission of any one of the four types of phonons is possible, but the ones with the shortest interaction times are favored, and the natural priority in typical semiconductors is therefore LO, TO, LA, TA. In the plasmon decay curve, LO phonon emission characterizes the initial sharp drop and TA phonon collision accounts for the slow tailing off. LA and TO phonon emissions are not important with respect to characterizing this curve.

It is understood that a highly polished metal surface that reflects light offers poor light penetration, and thus conversely, a rough surface is better for coupling light (e.g. a laser) into. Generally speaking, a rough surface having a periodic surface topography morphology will tend to act as a grating to match the phase of incident light as well as enhance the light to penetrate the surface and be absorbed in the metal. Thus, the generation of a plasmon is highly dependent on the roughness of the conductive surface.

Figure 3:
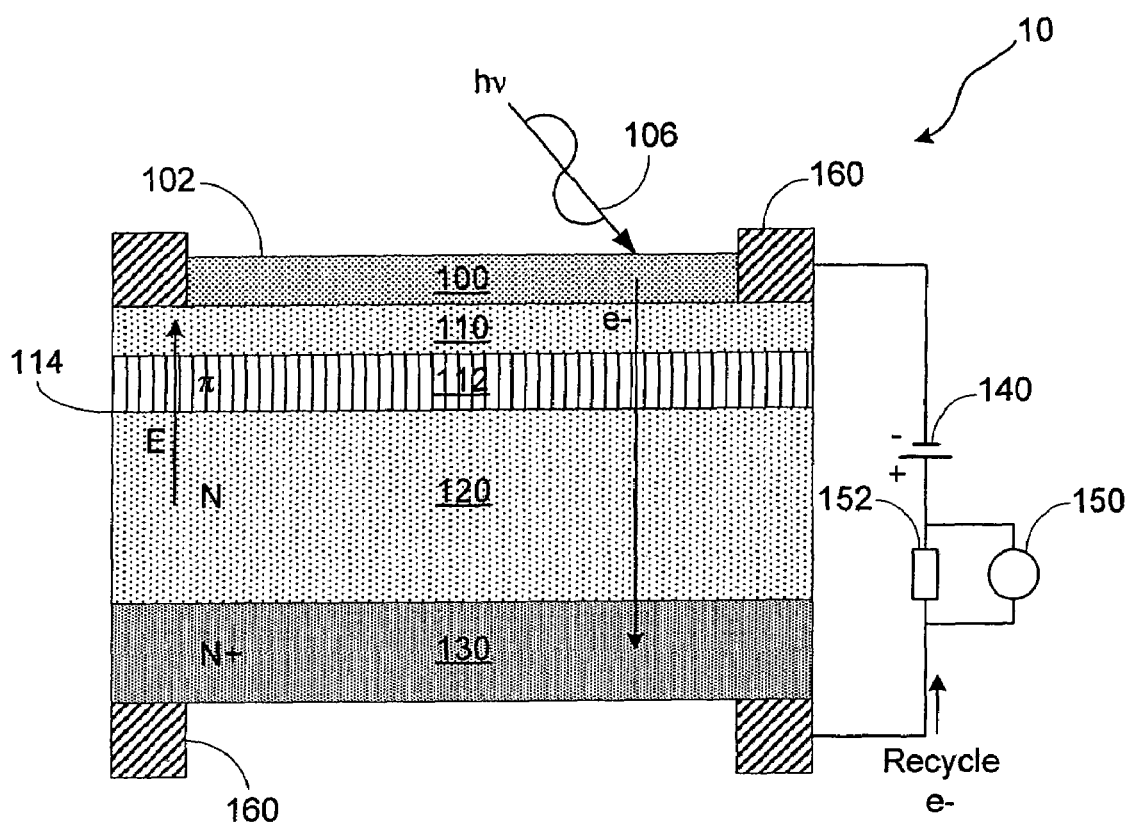
FIG. 3 is a functional block diagram, not drawn to scale, of a detector according to the present disclosure.

With reference now to FIG. 3, the present disclosure addresses solutions to the problems encountered by conventional surface roughness detectors by monitoring the high-energy electrons produced by the decay of a plasmon induced in the material of interest. Thus, with continued reference to FIG. 3, one embodiment of a detector 10 according to the present disclosure includes two "polaron"

active layers 110 and 112 (a metal light shield and a polaron buffer), with the metal layer 100 of interest deposited on the metal light shield 110. Gold and silver are materials known to have suitable characteristics for use in the present detector as metal layer 100, but other materials are also contemplated herein. A laser beam 106 can then be impinged onto the surface 102 of the deposited metal layer 100 to induce the formation of a plasmon therein.

The metal light shield layer 110 is selected to slow the high-energy electrons emitted by the decay of this plasmon to thermal electrons through the generation of polarons. This layer further acts to block incident and ambient light and thus prevent light from reaching the underlying layers, which may be photoconductive. The polaron buffer layer 112 is selected to slow the high-energy electrons emitted by the decaying plasmon to thermal energy levels through the generation of polarons, and is most preferably a so-called pi ($\pi$) region (that is, an electric insulator substantially void of conducting host electrons or holes, and may be, for example, lightly doped P silicon). Thermal electrons cannot traverse across this region, but the high-energy decay electrons, due to their concentration gradient high momentum, can diffuse through and traverse such a region. An applied electric field E acts to collimate the polarons vertically downward towards a collector junction 114 (described below). Materials suitable for use in the polaron buffer layer include, among others, ZnSe, CdS, GaP, GaAs, and Si. Assuming an average polaron velocity of $10^6$ m/sec the thickness of the polaron buffer layer 112 would typically need to be about 1 µm for LO phonon emission. The thickness of the light shield layer 110 would typically also be in the micron range, as dictated by the material used and the ambient light wavelength. The choice of materials will be dictated by, among others, the type of phonons emitted, the energy of the decay electrons, and the purity and perfection of the crystals used.

With continued reference to FIG. 3, a collector junction 114 underlies and is formed by the polaron buffer layer 112 and an N collector layer 120 to capture the thermal electrons cooled down by the polaron buffer layer. The collector junction is preferably a hetero junction, bound by a semiconductor material having a polar or ionic nature such as ZeSe, CdS, GaP, and GaN (which are sensitive to ultraviolet and visible light), CdSe and GaAs (which are sensitive to light in the infrared spectrum), or a non-polar semiconductor such as Si. It must be noted that homo junctions (that is, junctions formed between two layers of the same material but having different doping) are also applicable. The main function of the collector junction is to remove heat and energy from the hot electrons and thereby enrich polaron formation and decay, and convert the electron flow from a diffusion current propagated by the electrons' concentration gradient to a drift current propagated by the applied bias voltage discussed in greater detail below. Both flows consist of thermal electrons, and as described below the drift current continues to flow and be recycled through an external circuit.

As mentioned, the semiconductor substrate layer 120 (made of, for example, moderately doped N silicon) underlies the collector junction 114, and a higher-doping degenerate semiconductor layer 130 underlies the semiconductor substrate layer 120. The thermal electrons exiting the polaron buffer layer 112 form an electrical output current e− through the collector junction 114 and semiconductor layers 120, 130 (which act as N− type collector and degenerate N+ ohmic contact, respectively) that is supplied to an external current measurement device such as oscilloscope 150 (shown connected in parallel to a non-inductive load 152, such as a resistor). This current may then be further be "recycled" through an external circuit 140 that sends it back to the plasmon layer 100 to form new polarons in the next cycle of plasmon decay. Ohmic contacts or electrodes 160 provided at the metal layer and semiconductor layers allow recycling the output current e− as well as applying the electric field E such as through a battery providing a dc bias.

The output current e− may be enhanced at the collector junction through several means, such as avalanche multiplication. To enhance the output current, the materials and nanostructures of the polaron buffer layer 112 and collector junction 114 may be selected to be optimally matched so that the thermal electrons arrive at the collector junction with sufficient energy to maximize the output current.

It will be appreciated by the skilled reader that the present disclosure is directed to a novel method and device for detecting and monitoring surface roughness that avoid the problems found in current state of the art methods and devices. By detecting the output current generated by the plasmon decay electrons, changes in the surface roughness may be monitored. Furthermore, given the incident laser beam wavelength, the metal deposited, and surface pattern and roughness density, the input power density may be derived. The responsivity of the detector 10 is defined as the output current divided by this input power density, and thus by analyzing the signal to noise ratio of the output current and the conversion efficiency of photons to plasmons, the relationship of the surface roughness to output current may be derived.

While several illustrative embodiments of the invention have been shown and described, numerous variations and alternative embodiments will occur to those skilled in the art. The relative thicknesses of the various layers in FIG. 3, for instance, are not to be understood as disclosing a preferred or necessary thickness ratio among these layers. Such variations and alternative embodiments are contemplated, and can be made without departing from the scope of the invention as defined in the appended claims.

What is claimed is:

1. A method for monitoring the surface roughness of a metal, comprising:
    impinging a laser beam onto the surface of a metal layer to induce the formation of a plasmon therein; and
    monitoring a current of decay electrons emitted by the plasmon.

2. The method of claim 1, wherein monitoring the current further comprises:
    collecting the decay electrons.

3. The method of claim 2, further comprising:
    slowing the decay electrons to thermal energy levels before collecting the decay electrons.

4. The method of claim 3, wherein slowing the decay electrons comprises:
    slowing the decay electrons in a buffer layer comprising a substantially non-conductive Π region.

5. The method of claim 4, further comprising:
    passing the decay electrons through a layer of substantially non-light transmissive material prior to collecting them.

6. The method of claim 4, wherein the buffer layer comprises any one or more of the group consisting of ZnSe, GaP, GaAs, and Si.

7. The method of claim 2, wherein collecting the decay electrons comprises:
    collecting the decay electrons at a collector junction.

8. The method of claim 2, wherein collecting the decay electrons comprises:

collecting the decay electrons at a semiconductor layer.

9. The method of claim 8, wherein monitoring the current further comprises:

conducting the current to the metal layer through an electric circuit connected between the semiconductor layer and the metal layer.

* * * * *